US00PP35525P2

(12) United States Plant Patent
Hartman

(10) Patent No.: US PP35,525 P2
(45) Date of Patent: Dec. 5, 2023

(54) ***CALADIUM* PLANT NAMED 'BRZ STR 013-22173'**

(50) Latin Name: ***Caladium* X *hortulanum***
Varietal Denomination: BRZ STR 013-22173

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 18/121,498

(22) Filed: Mar. 14, 2023

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
CPC ... A01H 5/12; A01H 5/00; A01H 5/02; A01H 6/10
See application file for complete search history.

(56) References Cited

U.S. PATENT DOCUMENTS

PP25,421 P2 * 4/2015 Hartman ..... A01H 5/02 Plt./373
PP31,276 P2 * 12/2019 Hartman ..... A01H 5/12 Plt./373

* cited by examiner

*Primary Examiner* — June Hwu
(74) *Attorney, Agent, or Firm* — C. Anne Whealy

(57) ABSTRACT

A new and distinct cultivar of *Caladium* plant named 'BRZ STR 013-22173', characterized by its intermediate height and upright to mounding plant habit; dense, leafy and bushy appearance; vigorous growth habit and rapid growth rate; lance-type leaves that are reddish bronze to dark orange in color with variable and random pink-colored spots; intervenous and leaf notch areas may be tinged with green especially on plants that have not been de-eyed; and petioles that are tan in color with faint brown-colored stippling, streaks and tessellations.

4 Drawing Sheets

Figure 1:
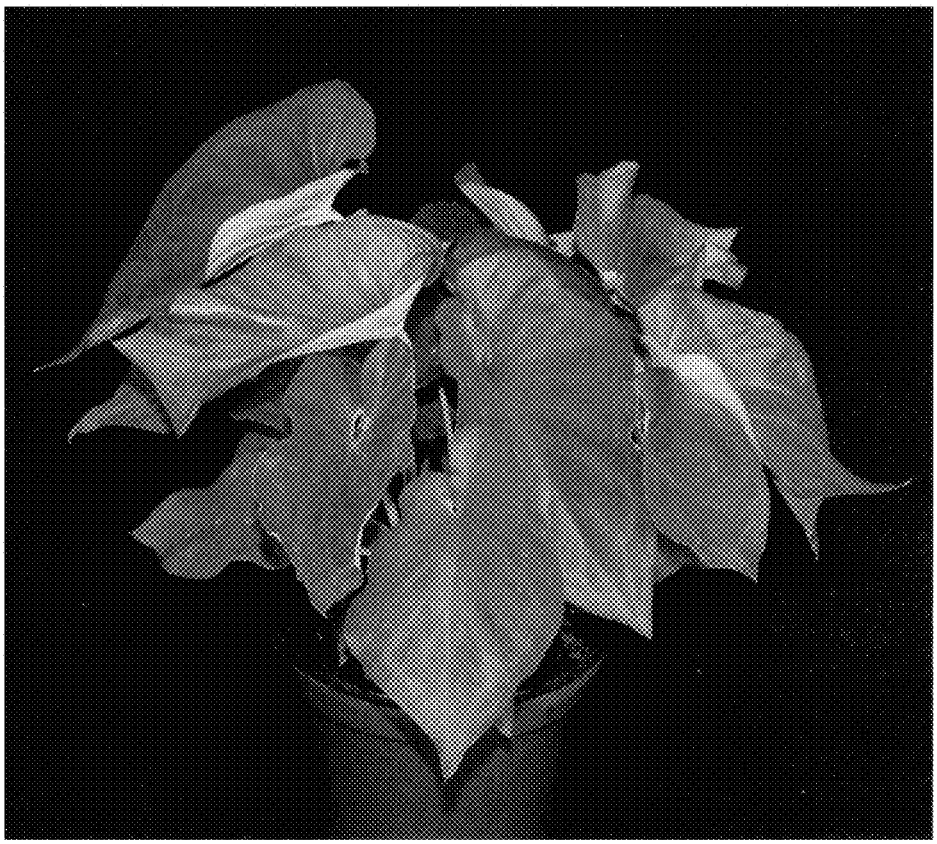

Botanical designation: *Caladium* X *hortulanum*.
Cultivar denomination: 'BRZ STR 013-22173'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Caladium* plant, botanically known as *Caladium* X *hortulanum*, commercially referred to as a lance leaf-type *Caladium* and hereinafter referred to by the name 'BRZ STR 013-22173'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2012 in Avon Park, Fla. of *Caladium* X *hortulanum* 'Desert Sunset', disclosed in U.S. Plant Pat. No. 25,421, as the female, or seed, parent with *Caladium* X *hortulanum* 'Red Flash', not patented, as the male, or pollen, parent. The new *Caladium* plant was discovered and selected by the Inventor as a single plant within the progeny of the stated cross-pollination in a controlled outdoor nursery environment in Avon Park, Fla. in September, 2013.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2014 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BRZ STR 013-22173'. These characteristics in combination distinguish 'BRZ STR 013-22173' as a new and distinct *Caladium* plant:

1. Intermediate in height and upright to mounding plant habit; dense, leafy and bushy appearance.
2. Vigorous growth habit and rapid growth rate.

3. Lance-type leaves that are reddish bronze to dark orange in color with variable and random pink-colored spots; intervenous and leaf notch areas may be tinged with green especially on plants that have not been de-eyed.
4. Petioles that are tan in color with faint brown-colored stippling, streaks and tessellations.

Plants of the new *Caladium* differ primarily from plants of the female parent, 'Desert Sunset', in the following characteristics:

1. Leaves of plants of the new *Caladium* are reddish bronze to dark orange in color with variable and random pink-colored spots whereas leaves of plants of 'Desert Sunset' are bronze salmon pink in color with darker-colored venation.
2. Leaf petioles of plants of the new *Caladium* are tan in color with faint brown-colored stippling, streaks and tessellations whereas leaf petioles of plants of 'Desert Sunset' are tannish green in color with greenish brown-colored stippling and stripes.

Plants of the new *Caladium* differ primarily from plants of the male parent, 'Red Flash', in the following characteristics:

1. Plants of the new *Caladium* are shorter than plants of 'Red Flash'.
2. Plants of the new *Caladium* produce finished plants in 15-cm containers about one to three weeks earlier than plants of 'Red Flash'.
3. Plants of the new *Caladium* have lance-types leaves whereas plants of 'Red Flash' have fancy-type leaves.
4. Leaves of plants of the new *Caladium* are reddish bronze to dark orange in color with variable and random pink-colored spots whereas leaves of plants of 'Red Flash' have red-colored venation and intervenous areas with pink and white-colored spots and dark green-colored borders.
5. Leaf petioles of plants of the new *Caladium* are tan in color with faint brown-colored stippling, streaks and tessellations whereas leaf petioles of plants of 'Red Flash' are reddish pink to tannish pink in color with darker-colored stippling and stripes.

Plants of the new *Caladium* can be compared to plants of *Caladium* X *hortulanum* 'Bold 'N Beautiful', disclosed in U.S. Plant Pat. No. 30,696. In side-by-side comparisons, plants of the new *Caladium* differ primarily from plants of 'Bold 'N Beautiful' in the following characteristics:

1. Plants of the new *Caladium* are more upright than and not as mounding as plants of 'Bold 'N Beautiful'.
2. Leaves of plants of the new *Caladium* are reddish bronze to dark orange in color with variable and random pink-colored spots whereas leaves of plants of 'Bold 'N Beautiful' have dark green-colored margins, transitional areas that are white and dark green mosaic, reddish pink-colored venation and the areas adjacent to the veins and intervenous areas that are pinkish red in color; with high light conditions, intervenous areas can be mostly white and/or greenish white variably tinged with purplish or pinkish red.
3. Leaf petioles ofplants of the new *Caladium* are tan in color with faint brown-colored stippling, streaks and tessellations whereas leaf petioles of plants of 'Bold 'N Beautiful' are blackish green in color with tan orange-colored stripes, streaks and tessellations.

Plants of the new *Caladium* can also be compared to plants of *Caladium* X *hortulanum* 'Berries N'Burgundy', disclosed in U.S. Plant Pat. No. 28,650. In side-by-side comparisons, plants of the new *Caladium* differ primarily from plants of 'Berries N'Burgundy' in the following characteristics:

1. Plants of the new *Caladium* produce finished plants in 15-cm containers about one to three weeks earlier than plants of 'Berries N' Burgundy'.
2. Plants of the new *Caladium* have lance-types leaves whereas plants of 'Berries N'Burgundy' have fancy-type leaves.
3. Leaves of plants of the new *Caladium* are reddish bronze to dark orange in color with variable and random pink-colored spots whereas leaves of plants of 'Berries N'Burgundy' are dark green in color overlain with a variable reddish bronze cast; areas surrounding the midvein and lateral veins are variably suffused with grey green-colored flecks with red orange to coral pink-colored veins.
4. Leaf petioles of plants of the new *Caladium* are tan in color with faint brown-colored stippling, streaks and tessellations whereas leaf petioles of plants of 'Berries N' Burgundy' are pink in color with brown-colored stippling, streaks and stripes.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'BRZ STR 013-22173' grown in a container that has had its tuber de-eyed prior to planting.

Figure 2:
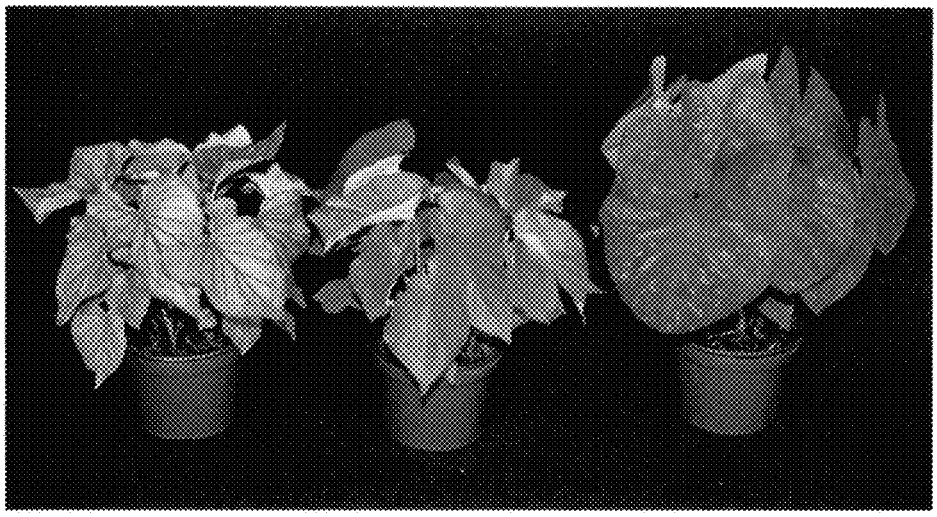

The photograph at the top of the second sheet (FIG. 2) is side perspective view of typical plants of the female parent, 'Desert Sunset' (left), 'BRZ STR 013-22173' (center) and the male parent, 'Red Flash' (right).

Figure 3:
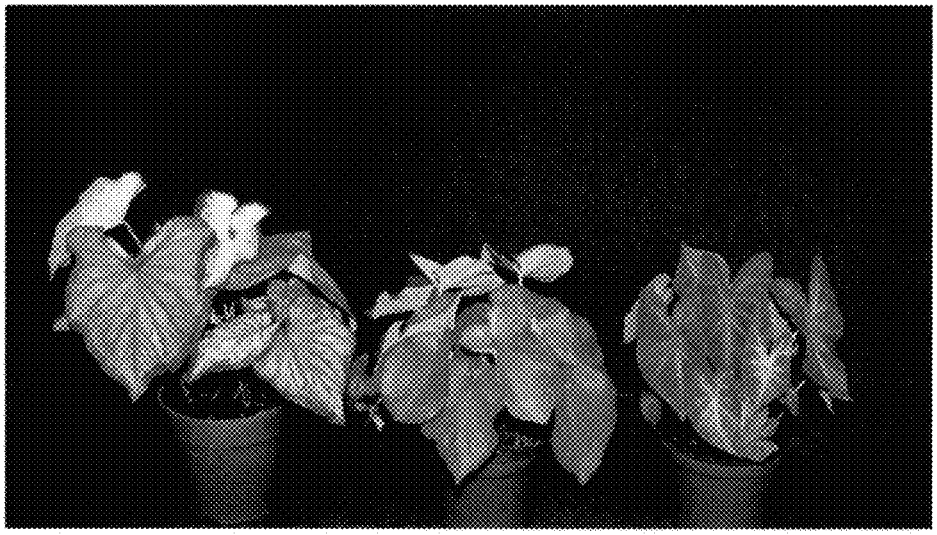

The photograph at the bottom of the second sheet (FIG. 3) is side perspective view of typical plants of 'Bold 'N Beautiful' (left), 'BRZ STR 013-22173' (center) and 'Berries N'Burgundy' (right).

Figure 4:
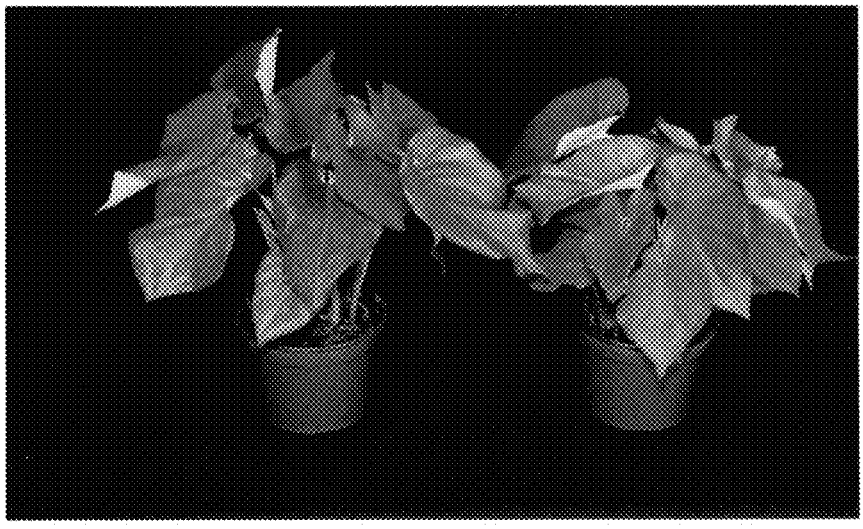

The photograph at the top of the third sheet (FIG. 4) is a comparison view of typical plants of 'BRZ STR 013-22173' grown in containers, the plant on the left has not had its tuber de-eyed and the plant on the right has had its tuber de-eyed prior to planting.

Figure 5:
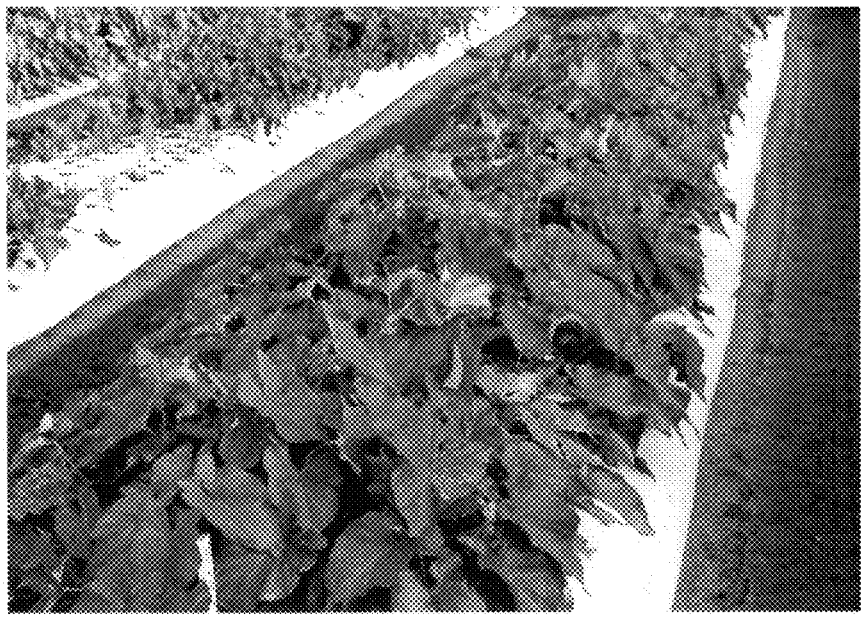

The photograph at the bottom of the third sheet (FIG. 5) is a side perspective view of typical plants of 'BRZ STR 013-22173' grown in an open production field.

Figure 6:
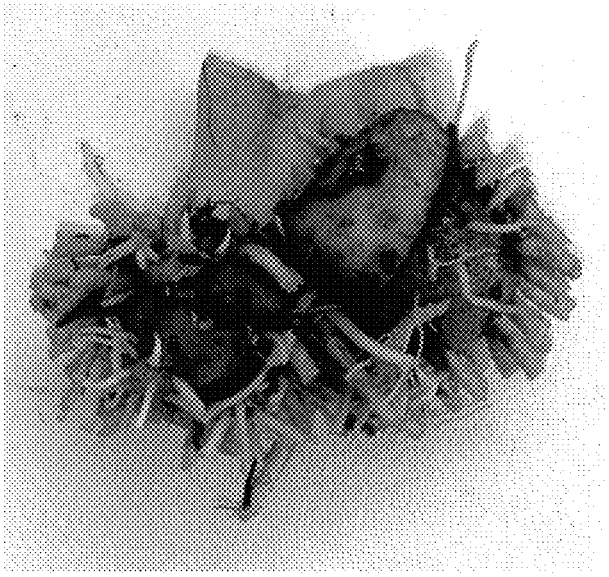

The photograph at the top of the fourth sheet (FIG. 6) is a close-up view of typical freshly-harvested tubers with roots and leaf petioles of 'BRZ STR 013-22173'.

Figure 7:
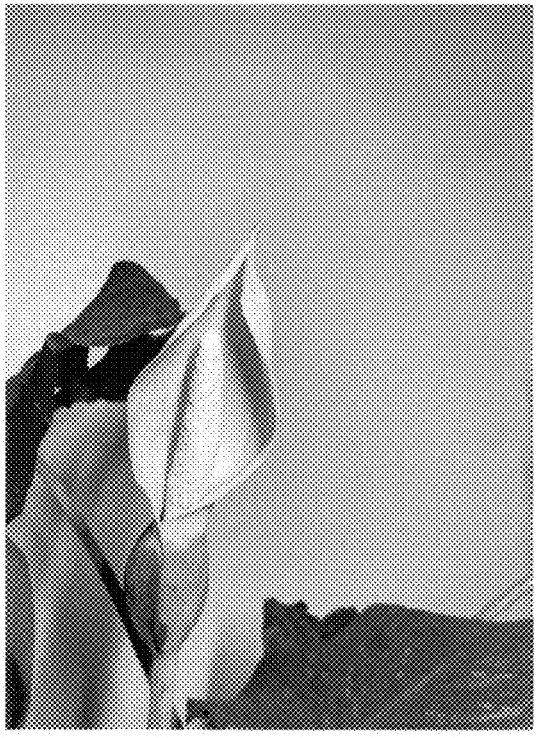

The photograph at the bottom of the fourth sheet (FIG. 7) is a close-up view of a typical inflorescence of 'BRZ STR 013-22173'.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28C to 33C, night temperatures ranged from about 22C to 25C and light levels were about 1,300 μmol. During the production of the outdoor nursery-grown plants, day temperatures ranged from about 29C to 35C, night temperatures ranged from about 23C to 26C and full sunlight conditions. Plants grown in the shade house were seven weeks old and plants grown in the outdoor nursery were 5.5 months old when the photographs and the detailed description were taken. In the following description, color references are made to The Royal Horticultural Society Colour Chart, 2001 and 2015 Editions, except where general terms of ordinary dictionary significance are used.

Botanical classification: *Caladium* X *hortulanum* 'BRZ STR 013-22173'.

Parentage:

*Female, or seed, parent.*—*Caladium* X *hortulanum* 'Desert Sunset', disclosed in U.S. Plant Pat. No. 25,421.

*Male, or pollen, parent.*—*Caladium* X *hortulanum* 'Red Flash', not patented.

Propagation:

*Type.*—By "chipping" the tubers.

*Time to initiate roots, summer.*—About seven to ten days at temperatures about 32C.

*Time to initiate roots, winter.*—About two to three weeks at temperatures about 24C.

*Tuber description* (*outdoor nursery-grown plants*).—Appearance: Multi-segmented; individual segments are elliptic to irregular in shape. Height: About 2.3 cm to 3 cm. Diameter: About 3.4 cm to 7.6 cm. Segment height: About 2.3 cm to 3 cm. Segment diameter: About 1.2 cm to 3.8 cm. Axillary bud shape: Roughly triangular. Axillary bud height: About 5 mm. Axillary bud width: About 3 mm. Texture: Thick, starchy; somewhat brittle. Color: Periderm, freshly-harvested: Close to 200D. Periderm, dried: Close to 200A. Epidermis: Close to 159B to 159C becoming closer to 199D with subsequent development. Cortical tissue: Close to 11D. Axillary buds: Close to 37D. Root description: Thick, fleshy contractile roots with few lateral branches; color, close to N155D, actual color of the roots is dependent on substrate composition, water quality, fertilizer type and formulation, substrate temperature and physiological age of roots. Rooting density: Dense.

Plant description:

*Plant type.*—Herbaceous perennial; suitable as a potted plant in containers 15-cm to 25-cm and suitable as a landscape plant in shaded areas.

*Plant and growth habit.*—Intermediate in height and upright to mounding plant habit; dense, leafy and bushy appearance; vigorous growth habit and rapid growth rate; potted plants finish in saleable form in about seven weeks after planting tubers; leaf petioles and leaves arise from one or more growing points on tubers; leaf petioles initially upright and leaning and arching outwardly with development.

*Plant height, from soil level to top of foliar plane, shade house-grown potted plants.*—About 21 cm to 26 cm.

*Plant height, from soil level to top of floral plane, shade house-grown potted plants.*—About 24 cm.

*Plant diameter, shade house-grown potted plants.*—About 34 cm to 39 cm.

*Number of shoots per plant, shade house-grown potted plants, tubers not de-eyed.*—About three to five develop per #1 tuber.

*Number of shoots per plant, shade house-grown potted plants, tubers de-eyed.*—About eight to nine develop per #1 tuber.

*Cataphylls, shade house-grown potted plants.*—Length: About 3 cm to 9 cm. Width: About 1.3 cm to 1.6 cm. Shape: Wedge-shaped. Apex: Acute to acuminate or emarginate. Base: Sheathing the stem. Texture, outer and inner surfaces: Smooth, glabrous. Color, outer surface: Close to N170D occasionally tinged with 147C; streaked and stippled with close to 200B; color becoming closer to 200D with subsequent development. Color, inner surface: Close to N155D with colors and color patterns visible from outer surface.

Leaf description:

*Arrangement and type.*—Alternate; simple; lance-type.

*Length, shade house-grown potted plants.*—About 14 cm to 22 cm.

*Width, shade house-grown potted plants.*—About 9.5 to 12.5 cm; when flattened, about 11.2 cm to 13 cm.

*Shape.*—Ovate to cordate.

*Apex.*—Acute to acuminate.

*Base.*—Sagittate-peltate; cordate.

*Margin.*—Entire; mostly flat to somewhat wavy with broad undulations.

*Texture and luster, upper surface.*—Smooth, glabrous; thin; dull to somewhat metallic sheen.

*Texture and luster, lower surface.*—Smooth, glabrous; glaucous and dull; developing leaves may have a slightly metallic sheen.

*Venation pattern.*—Pinnate and palmate.

*Color, shade house-grown potted plants.*—When developing and fully expanded leaves, upper surface: Background color: Variable, close to 178A, 178B, 183A and/or 185A; occasionally tinged with close to 147A to 147B. Margins: Similar to background color; edge, close to 183A. Basal notch: Close to 185A and 53A; may also have sectors, close to 147A and 147C to 147D. Midvein: Close to 147B to 147C flushed with close to 183B or 178A; areas surrounding veins, close to 179A. Lateral venation: Close to 183A and 183B, may be tinged with close to 147B to 147C; areas surrounding veins, close to 179A. Spots: Close to 51C. When developing and fully expanded leaves, lower surface: Background color: Close to 195A tinged with close to N170D, may be faintly tinged with close to N186C. Margins: Close to 183A. Basal notch: Close to 185A. Midvein: Close to 196C variably flushed with close to 200D. Lateral venation: Close to 199C and 199D, areas surrounding veins may be close to 159C. Spots: Close to 39D.

*Petioles.*—Aspect: Initially upright and straight and somewhat leaning and arching outwardly with development; flexible. Length, shade house-grown potted plants: About 18 cm to 26 cm. Diameter, distally, shade house-grown potted plants: About 3 mm to 3.5 mm. Diameter, proximally, shade house-grown potted plants: About 4 mm to 5.5 mm. Texture and luster: Smooth, glabrous; distally, glaucous. Color, shade house-grown potted plants: Close to N170D, 195C, 199C and/or 199D; faintly stippled, streaked and tessellated with close to 200C and 200D; just below the leaf junction, close to 156D tinged with close to 181C and 181D and faintly and variably stippled, streaked and tessellated with close to 199A and 181C. Wing length, shade house-grown potted plants: About 4 cm to 6.5 cm. Wing diameter, shade house-grown potted plants: About 5 mm. Texture and luster, inner and outer surfaces: Smooth, glabrous; dull to slightly glossy. Wing color, shade house-grown potted plants: Outer surface: Close to N170D variably tinged with close to 147C and 147D; stippled, streaked and tessellated with close to 200B. Inner surface: Close to N155D; colors and patterns on the outer surface are visible on the inner surface.

Inflorescence description:

*Inflorescence arrangement.*—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance.*—Night-fragrant; jasmine-like with camphor note.

*Natural flowering season and flower longevity.*—Plants of the new *Caladium* typically flower during the spring and summer in central Florida; flowers develop about two weeks after growth commences; inflorescences last about three days before fading; inflorescences persistent.

*Spathe.*—Length, overall: About 10.4 cm. Length, distal open portion: About 6.9 cm. Length, proximal closed portion: About 3.5 cm. Width, distal open portion: About 3.2 cm. Depth, distal open portion: About 1.4 cm. Width, at constriction: About 1.2 cm. Width, proximal closed portion: About 2.1 cm. Shape, open portion: Ovate. Apex: Acute to acuminate. Base: Acute. Margin: Entire; slightly reflexed. Texture and luster, front surface: Smooth, glabrous; dull sheen. Texture and luster, rear surface: Smooth, glabrous; dull sheen; proximally, glaucous. Color, front surface: Distal open portion: Close to 155D; towards the margins, faintly tinged with close to N155C; with subsequent development, distally becoming closer to 199A and 200D. Proximal closed portion: Close to 148D; towards the base, flushed with close to 187A; color does not change with subsequent development. Color, rear surface: Distal open portion: Close to 157A and 145D; center, close to 145C tinged with close to 146D; color does not change with subsequent development. Proximal closed portion: Close to 147D and 138B; color does not change with subsequent development.

*Spadix.*—Length, overall: About 6.9 cm. Length, male flower zone: About 4 cm. Length, sterile zone: About 1.6 cm. Length, female flower zone: About 1.3 cm. Diameter, male flower zone: About 9 mm. Diameter, sterile flower zone: About 6 mm. Diameter, female flower zone: About 7 mm. Shape: Columnar, spindle-shaped. Apex: Bluntly rounded, obtuse. Base: Obtuse. Aspect: Upright. Color, mature, male zone: Close to 158D. Color, mature, sterile zone: Close to 158D. Color, mature, female zone: Close to 155B and 158A. Male flowers: Quantity per spadix: About 144. Shape: Obovate. Height: About 3 mm to 4 mm. Diameter: About 3 mm to 3.5 mm. Pollen amount: Abundant. Pollen color: Close to 10C. Female flowers: Quantity per spadix: About 105. Shape: Obovate. Height: About 2.5 mm to 3 mm. Diameter: About 2 mm. Stigma color: Close to 155B. Ovary color: Close to 158A.

*Scapes.*—Length: About 13.6 cm. Diameter: About 4 mm. Strength: Sturdy; somewhat flexible. Aspect: Mostly erect, straight. Texture and luster: Smooth, glabrous; proximally, slightly glossy and distally, glaucous. Color: Close to 147C flushed with close to 199B and 200D; just below spathe, close to 147C and 146B tinged with close to 199B.

*Seeds and fruits.*—To date, seed and fruit development have not been observed on plants of the new *Caladium*.

Pathogen tolerance/resistance: Plants of the new *Caladium* have been observed to have average tolerance to *Pythium* Root Rot and average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate emperatures ranging from about 7C to about 40C and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'BRZ STR 013-22173' as illustrated and described.

* * * * *